(12) United States Patent
Cunningham et al.

(10) Patent No.: US 7,528,112 B2
(45) Date of Patent: May 5, 2009

(54) SMALL SURVIVAL-PROMOTING/ IMMUNOMODULATORY PEPTIDE FOR TREATMENT OF BRAIN DAMAGE, NEURODEGENERATIVE DISORDERS, AND INFLAMMATORY DISORDERS

(75) Inventors: Timothy J. Cunningham, Fort Washington, PA (US); Lihua Yao, Edgevale, PA (US)

(73) Assignee: Drexel University, Philadelphia, PA (US)

( * ) Notice: Subject to any disclaimer, the term of this patent is extended or adjusted under 35 U.S.C. 154(b) by 709 days.

(21) Appl. No.: 10/714,699

(22) Filed: Nov. 17, 2003

(65) Prior Publication Data

US 2004/0132665 A1 Jul. 8, 2004

Related U.S. Application Data

(60) Provisional application No. 60/426,536, filed on Nov. 15, 2002.

(51) Int. Cl.
*A61K 38/08* (2006.01)
*C07K 7/06* (2006.01)

(52) U.S. Cl. .......................................... 514/15; 530/328
(58) Field of Classification Search ........................ None
See application file for complete search history.

(56) References Cited

U.S. PATENT DOCUMENTS 6,262,024 B1 7/2001 Cunningham et al.

OTHER PUBLICATIONS

Jackowski, British Journal of Neurosurgery 9: (1995) 303-317.*
Rudinger, In "Peptide Hormones" (ed., J.A. Parsons) University Park Press, Baltimore, pp. 1-7 (1976).*
Mihelich et al., Structure-based design of a new class of anti-inflammatory drugs: secretory phospholipase $A_2$ Inhibitors, SPI, Biochimica et Biophysica Acta 1441 (1999), pp. 223-228.
Springer, D, An Update on Inhibitors of Human 14kDa Type II s-$PLA_2$ in Development, Current Pharmaceutical Design (2001), vol. 7, pp. 181-198.
Abraham et al., Efficacy and safety of LY315920Na/S-5920, a selective inhibitor of 14-kDa group IIa secretory phospholipase $A_2$, in patients with suspected sepsis and organ failure, Criticial Care Medicine, (2003) vol. 31, No. 3, pp. 718-728.
Eagleson, et al., Rescue of Both Rapidly and Slowly Degenerating Neurons in the Dorsal Lateral Geniculate Nucleus of Adult Rats by a Cortically Derived Neuron Survival Factor, Experimental Neurology, (1992) vol. 116, pp. 156-162.
Eagleson et al., Different Populations of Dorsal Lateral Geniculate Nucleus Neurons Have Concentration-Specific Requirements for a Cortically Derived Neuron Survival Factor, Experimental Neurology, (1990), vol. 110: pp. 284-290.
Paterson et al., $\alpha$-Cardiac Actin is the Major Sarcomeric Isoform Expressed in Embryonic Avian Skeletal Muscle, Science (1984), vol. 224, pp. 1436-1438.
Cunningham et al., Identification of a Survival-Promoting Peptide in Medium Conditioned by Oxidatively Stressed Cell Lines of Nervous System Origin, The Journal of Neuroscience (1998), vol. 18, No. 18., pp. 7047-7060.
Cunningham et al., Identification of the Human cDNA for New Survival/Evasion Peptide (DSEP): Studies in Vitro and in Vivo of Overexpression by Neural Cells, Experimental Neurology (20002), vol. 177, pp. 32-39.
Cunningham et al., Calreticulin Binding and Other Biological Activities of Survival Peptide Y-P30 Including Effects of Systemic Treatment of Rats, Experimental Neurology (2000), vol. 163, pp. 457-468.
Cunningham, et al., 2006, J. Neuroinflammation 3:25.
Westley, et al., 1996, J. Biol. Chem., 271:5347-5352.

* cited by examiner

*Primary Examiner*—Robert C Hayes
(74) *Attorney, Agent, or Firm*—Drinker Biddle & Reath, LLP

(57) ABSTRACT

A synthetic peptide sequence demonstrating neuroprotective and anti-inflammatory functions is disclosed. Methods of use for the synthetic peptide are also provided.

3 Claims, 6 Drawing Sheets

SMALL SURVIVAL-PROMOTING/ IMMUNOMODULATORY PEPTIDE FOR TREATMENT OF BRAIN DAMAGE, NEURODEGENERATIVE DISORDERS, AND INFLAMMATORY DISORDERS

This application claims priority to U.S. Provisional Application 60/426,536, filed Nov. 15, 2002, the entire contents of which are incorporated herein by reference.

Pursuant to 35 U.S.C. §202(c), is acknowledged that the U.S. Government has certain rights in the invention described, which was made in part with funds from NIH grant number NS16347, from the National Institute of Neurological Disorders and Stroke.

FIELD OF THE INVENTION

The present invention relates to a composition of matter comprising a small peptide, for promoting neurite outgrowth, enhancing survival of neuronal cells, and/or inhibiting phospholipase A2; to a pharmaceutical preparation containing the small peptide; and to its use in the treatment of neuron damage, neurodegenerative disorders, and neuronal and non-neuronal disorders with an inflammatory component.

BACKGROUND OF THE INVENTION

Several publications and patent documents are cited in this application in order to more fully describe the state of the art to which this invention pertains. The disclosure of each of these citations is incorporated by reference herein.

Neurotrophic factors are considered to be vital for normal development of the nervous system. During development, neuronal target structures produce limited amounts of specific neurotrophic factors necessary for both the survival and differentiation of neurons projecting into the structures. The same factors have been found to be involved in the survival and/or maintenance of mature neurons.

A neurotrophic factor is defined as a substance capable of increasing and/or maintaining survival of a neuron population, and possibly affecting outgrowth of neurites (neuron processes) and certain other metabolic activities of a neuron. Neurotrophic factors are generally described as soluble molecules synthesized in the peripheral targets of neurons and transported to their cell bodies, where they exert their effects.

Studies with isolated neurotrophic factors have shown that exogenously added neurotrophic factors can exert their neurotrophic effects upon cultured neurons in vitro, or by administration to damaged or degenerated neurons in vivo. For this reason, various neurotrophic factors have received great attention as potential therapeutic agents for treatment of degenerative diseases of the central nervous system, as well as traumatic damage to the CNS. For example, nerve growth factor (NGF) has been shown to increase the survival, function and regeneration of cholinergic neurons in the basal forebrain. Degeneration of this population of cholinergic neurons has been associated with patients having Alzheimer's disease, and could be the primary neuronal defect responsible for the loss of cognitive function associated with Alzheimer's disease. NGF has been found to be synthesized and released from the target areas of these cholinergic neurons in the hippocampus and neurocortex, both areas of the brain associated with learning and memory. See Springer, J. E., Drug News and Perspectives, 4: 394-99 (1991). As another example, a dopaminergic neurotrophic factor (DNTF) has been purified and characterized, and found to promote survival and neurite outgrowth of dopaminergic neurons of the substantia nigra. DNTF is considered a potentially valuable therapeutic agent for the treatment of Parkinson's disease which involves degeneration of dopaminergic motor neurons of the central nervous system (U.S. Pat. No. 5,215,969 to Springer et al., 1993).

It can be seen from the foregoing examples that neurotrophic factors are a valuable source of therapeutic agents for the treatment of neuron damage and neurodegenerative disease. However, the development of such factors as therapeutic agents can be problematic. For example, it is difficult to determine the specificity of an endogenous neurotrophic agent, i.e., whether different factors exist for different nervous system pathways, and which neuron populations in those pathways are affected by a factor. In fact, many identified neurotrophic agents have been shown to have a wide range of biological functions, acting on both central and peripheral neurons, as well as non-neuronal cells in vitro (e.g., polypeptide growth factors and ciliary neurotrophic factor, CNTF). In the central nervous system, with its complex interconnections and heterogeneous neuron types, it is difficult to determine which neurotrophic factors are effective on a particular neuronal population. This difficulty is further exacerbated by the fact that many of the neurotrophic factors that have been characterized have been found to be closely related to one another. For example, it is now known that NGF possesses amino acid sequence homology to brain-derived neurotrophic factor (BNDF), a protein with similar, but not identical, in vitro properties as NGF (Barde et al., EMBO J., 1: 549-53, 1982; Leibrock et al., Nature, 341: 149-52, 1989). In fact, NGF, BNDF and the neurotrophin (NT) series have been classified as members of a superfamily of neurotrophic factors (NGF superfamily). Because of their similarity in amino acid sequence (and hence nucleotide sequences encoding the factor), it has been difficult to develop nucleic acid or antibody probes that are specific for a particular member of the family. The lack of a specific means for identifying a particular neurotrophic factor has hindered the elucidation of particular neuronal populations affected by a specific factor.

An additional obstacle to developing neurotrophic factors as therapeutic agents for treatment of damaged neurons is that few in vivo models exist to study the survival-promoting activity of these factors in the central nervous system. In order to develop a neurotrophic factor as an effective therapeutic agent for the treatment of neuron degeneration, it is important to be able to determine where in the central nervous system the neurotrophic factor operates, whether the treatment with exogenous neurotrophic factor is effective, and the concentration of neurotrophic factor effective for imparting a therapeutic effect. Such an objective would best be accomplished with a neurotrophic factor that is identifiable and distinct from other factors, that is capable of exerting an effect on many different neuron populations, and for which in vivo models are available to test the efficacy of the neurotrophic factor on a specific neuron population.

The neuron survival-promoting peptide Y-P30 was originally identified in the secretions of neural cells (neuroblastoma and retinoblastoma) subjected to oxidative stress (Cunningham, et al. 1998). Partially purified fractions of conditioned culture medium were screened in vitro until the active Y-P30 peptide was identified—the synthetic version of this peptide was then tested in vitro and in vivo and found to support neural cells which were degenerating for a variety of reasons, including oxidative stress and central nervous system trauma (Cunningham, et al. 1998; 2000). This peptide was later confirmed to be part of an endogenous human polypeptide (~12 kiloDaltons) named DSEP after identification of the human cDNA encoding DSEP and the locus of the DSEP gene in human chromosomal region 12 q (Cunningham, et al. 2002). In that study, it was found that overexpression of the full length polypeptide in neural cells made them resistant to several forms of oxidative stress including that resulting from immune cell attack.

The contribution of inflammatory cells and their secretions to cell death after CNS injury or in neurodegenerative disorders is for the most part well established (Stoll, 1998). The principal immune cell participants in the response to traumatic CNS injury are monocyte derivatives (microglia/macrophages). These cells are the source of a number of inflammatory agents that may contribute to neuron death, including superoxide anion, nitric oxide, IL-1β, and TNFα (reviewed by Rothwell, et al 1996, Stoll et al 1998, Jander, et al 1998, 2000; and Turrin, et al 2001). TNFα is best known for its cytotoxic activity outside the nervous system, but also has pronounced toxic activity on neural cells after brain injury (Barone, et al, 1997; Lavine, et al 1998). Both overexpression of the full length DSEP molecule and application of Y-P30 inhibits the appearance and differentiation of macrophages and microglia (Cunningham et al. 1998, 2000, 2002).

Steriod anti-inflammatory drugs currently used to treat nervous system injury and other disorders with an inflammatory component operate in part by stimulating the production of endogenous inhibitors of phospholipases (A2) (PLA2) which are the enzymes responsible for the production of several lipid mediators of inflammation (Flower, R J et al. 1979). PLA2 enzymes and downstream participants in this pathway play a role in chronic neurodegenerative disorders including Alzheimer's disease (Farooqui A A, et al., 1999; Hull M, et al., 2002).

Therefore, a need exists in the art for identification and testing in vivo of new neurotrophic factors which are distinct from other factors, exert an effect on many different neurons, and/or which can act as PLA2 inhibitors, to facilitate the development of new therapies for neurodegenerative disorders and for other diseases with an inflammatory component.

SUMMARY OF THE INVENTION

In accordance with one aspect of the present invention, there is provided a synthetic peptide, CHEC-9, having the sequence of CHEASAAQC (SEQ ID NO: 1), or variants thereof, wherein the peptide promotes neuron survival, inhibits a brain's immune response to degenerating elements, and/or inhibits phospholipase A2. The peptide may be linear or cyclized.

In accordance with another aspect of the present invention, there is provided a pharmaceutical preparation comprising the synthetic peptide, CHEC-9.

In another aspect of the invention, there is provided a nucleic acid encoding a synthetic peptide, CHEC-9, having the sequence of CHEASAAQC (SEQ ID NO: 1), or variants thereof.

In yet another embodiment of the invention, there is an antibody or fragment thereof which is immunologically specific for a synthetic peptide, CHEC-9, having the sequence of CHEASAAQC (SEQ ID NO: 1), or variants thereof.

In accordance with yet another aspect of the present invention, there is provided a method for treating a patient having a neurodegenerative disorder by administering to the patient a therapeutically effective amount of CHEC-9. Such neurodegenerative disorders include, but are not limited to, (1) trauma, (2) stroke, (3) nonspecific anoxia (i.e., anoxia due to drowning, suffocation, etc.), (4) neurodegenerative diseases such as Alzheimer's disease, Parkinson's disease and amyotrophic lateral sclerosis (ALS); and (5) mental retardation syndromes associated with progressive neuronal degeneration (e.g., cerebral palsies).

In accordance with another aspect of the present invention, there is provided a method for treating a patient having a disorder with an inflammatory component, by administering to the patient a therapeutically effective amount of CHEC-9. Such disorders include, but are not limited to, (1) asthma; (2) autoimmune disorders; (3) allergies; (4) arthritis; and (5) any disorder which might benefit from treatment using a steroid or a phospholipase A2 inhibitor.

In accordance with yet another aspect of the invention, a kit is provided which facilitates administering or testing for the CHEC-9 peptide.

DETAILED DESCRIPTION OF THE INVENTION

Figure 1:
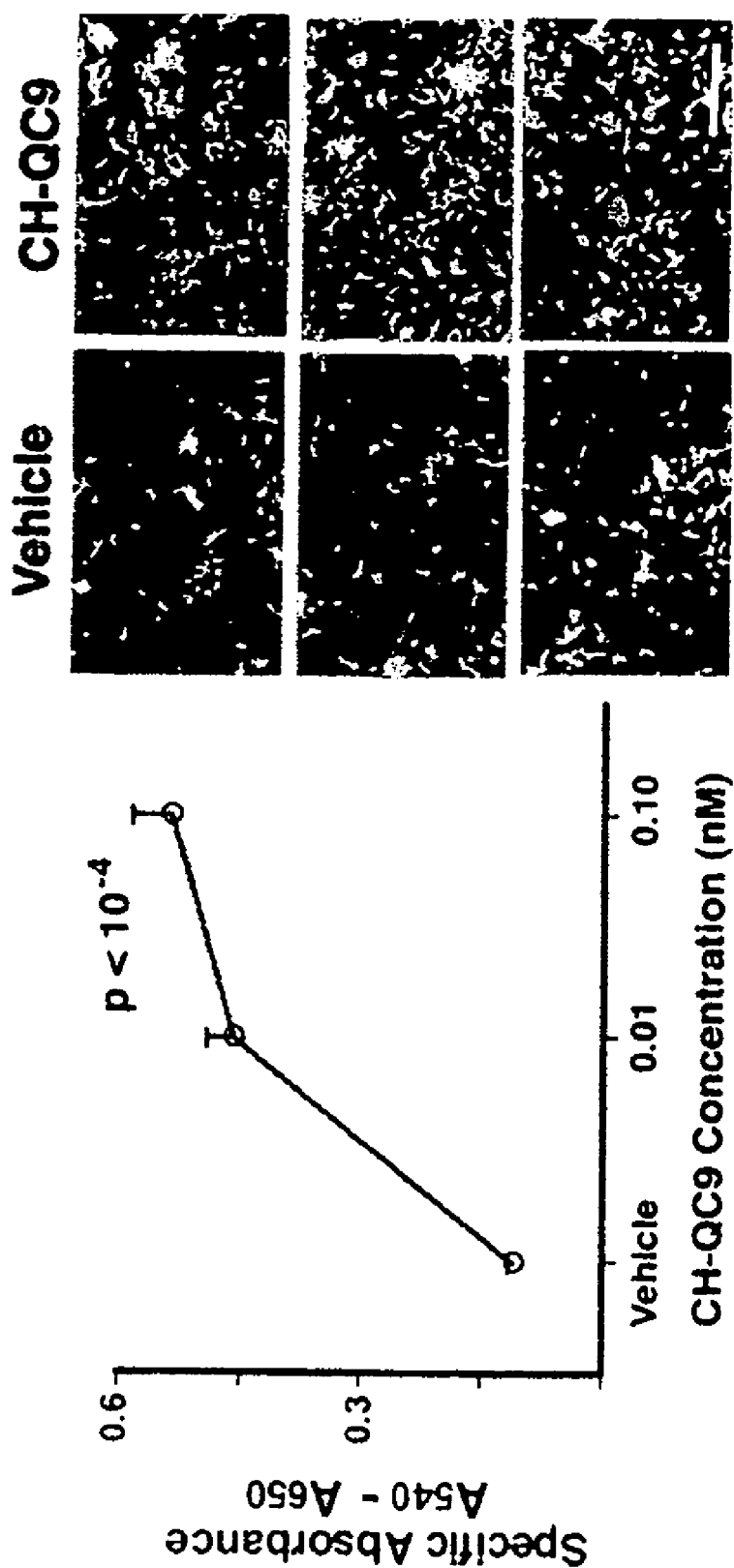
FIG. 1 shows increased survival of SY5Y neuroblastoma cells exposed to CHEC-9, following medium change and serum deprivation for 48 hrs. The cells were seeded at low density in serum and changed to serum free medium (with added CHEC-9 peptide or vehicle) after 2 hrs. Cell survival was measured with the WST electrocoupling reagent (Ocinda). The graph on the left shows increased CHEC-9 concentration correlates with increased cell survival. Three representative cultures from the 2 groups are shown in the panels on the right. Coomassie Blue stain. Bar=100 μm. (p value based on n=16 cultures for each condition in 2 separate experiments.)

A nine amino acid peptide CHEASAAQC (SEQ ID NO.: 1, designated CHEC-9 or CH-QC9) has been identified, synthesized and used to promote survival of neural cells in vitro and invivo, including after cerebral cortex injury. The peptide rescues neurons that would usually shrink, die or disintegrate following traumatic brain damage. Furthermore, the peptide possesses demonstrable phospholipase A2 inhibitory activity, and therefore has utility as a modulator of inflammation. A CHEC-9 peptide variant having the sequence CAHAQAESC (SEQ ID NO.: 2) also promotes survival of neural cells.

CHEC-9 constitutes an internal sequence of survival promoting peptide Y-P30 (U.S. Pat. No. 6,262,024). CHEC-9 and Y-P30 are derived from a 12 kiloDalton endogenous human protein, DSEP (GenBank Accession #AY044239, T. J. Cunningham, et al., 2002). CHEC-9 and Y-P30 differ from the sequence of DSEP in having a cysteine at position 23, instead of lysine. Like the larger peptides, CHEC-9 to promotes neuron survival and inhibits aspects of the immune response to cerebral cortex lesions, in particular the appearance and invasion of macrophages and microglia at the site of injury. Accordingly the peptide may be used for treatment of disorders involving acute neural degeneration (stroke and traumatic brain damage), as well as for treatment of several chronic neurodegenerative disorders including Alzheimer's disease. In the latter applications, CHEC-9 inhibits both neuron death and the brain's immune response to degenerating elements, which should slow the progress of these disorders and attendant decline of behavioral performance. Additionally, CHEC-9 inhibits phospholipase A2, and thus may be used to treat disorders associated with inflammation.

A "CHEC-9 peptide" is a peptide having the sequence of CHEASAAQC (SEQ ID NO: 1). The peptide may be linear or cyclic. The term "CHEC-9 peptide" may include variants of SEQ ID NO:1, wherein as few as 1 or as many as 9 amino acids are changed, provided that the peptide still promotes neuron survival, inhibits a brain's immune response to degenerating elements, and/or inhibits phospholipase A2. Variants may have mutations comprising insertions, deletions, or substitutions of amino acids. Variants preferably comprise conservative amino acid substitutions.

A "conservative amino acid substitution" as defined herein refers to replacement of an amino acid with a functionally and biochemically equivalent amino acid. These substitutions provide similar or enhanced function of a peptide. Functionally-equivalent amino acids are amino acids which share a common structure, side chain, polarity, and so forth. Examples of amino acids which may be functionally equivalent are:

| | |
|---|---|
| hydrophobic | Ala, His, Ile, Leu, Met, Phe, Trp, Tyr, Val |
| neutral hydrophilic | Cys, Ser, Thr |
| polar | Asn, Gln, Ser, Thr |
| acidic/negatively charged | Asp, Glu |
| charged | Arg, Asp, Glu, His, Lys |
| basic/positively charged | Arg, His, Lys |
| basic | Arg, Asn, Gln, His, Lys |
| residues that influence chain orientation | Gly, Pro |
| aromatic | His, Phe, Trp, Tyr |

An autoimmune disease is a disease which occurs when one or more components of the immune system targets the cells, tissues, and/or organs of a person's own body. Autoimmune diseases include, but are not limited to Multiple sclerosis, Myasthenia gravis, Autoimmune neuropathies such as Guillain-Barré, Autoimmune uveitis, Inflammatory Bowel Disease (including Crohn's Disease and Ulcerative colitis) Primary biliary cirrhosis, Autoimmune hepatitis, Type 1 or immune-mediated diabetes mellitus, Autoimmune thyroid disease (including Grave's Disease and Hashimoto's thyroiditis), Autoimmune oophoritis and orchitis, Autoimmune disease of the adrenal gland, Autoimmune hemolytic anemia, Pernicious anemia, Autoimmune thrombocytopenia, Temporal arteritis, Anti-phospholipid syndrome, Vasculitides such as Wegener's granulomatosis, Behcet's disease, Rheumatoid arthritis, Systemic lupus erythematosus, Scleroderma Polymyositis, dermatomyositis, Spondyloarthropathies such as ankylosing spondylitis, Sjogren's syndrome, Psoriasis, Dermatitis herpetiformis, Pemphigus vulgaris, and Vitiligo.

I. Preparation of Human CHEC-9-Encoding Nucleic Acid Molecules, CHEC-9 Peptides, and Antibodies Thereto Nucleic Acid Molecules: Nucleic acid molecules encoding CHEC-9 peptides of the invention may be prepared by two general methods: (1) synthesis from appropriate nucleotide triphosphates, or (2) isolation from biological sources. Both methods utilize protocols well known in the art. Preparation of an isolated nucleic acid molecule of the invention may be by oligonucleotide synthesis. The nucleic acid synthesized may be any combination of codons which encode the CHEC-9 peptide. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Alternatively, nucleic acid sequences encoding the CHEC-9 peptide may be isolated from appropriate biological sources using methods known in the art. Suitable probes for this purpose are derived from sequences which encode the amino acids of CHEC-9.

In accordance with the present invention, nucleic acids having the appropriate level of sequence homology with the CHEC-9 peptide may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m = 81.5° C. + 16.6 \log [Na+] + 0.41(\% G+C) - 0.63 (\% \text{formamide}) - 600/\#bp \text{ in duplex}$$

As an illustration of the above formula, using $[Na^+]=[0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell.

CHEC-9-encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention. As mentioned previously, such oligonucleotides are useful as probes for detecting or isolating CHEC-9 related nucleic acids.

It will be appreciated by persons skilled in the art that variants (e.g., allelic variants) of CHEC-9 sequences exist in the human population, and must be taken into account when designing and/or utilizing oligonucleotides of the invention. Accordingly, it is within the scope of the present invention to encompass such variants, with respect to the CHEC-9 sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a human population. The usage of different wobble codons and genetic polymorphisms which give rise to conservative or neutral amino acid substitutions in the encoded protein are examples of such variants.

Additionally, the term "substantially complementary" refers to oligonucleotide sequences that may not be perfectly matched to a target sequence, but such mismatches do not materially affect the ability of the oligonucleotide to hybridize with its target sequence under the conditions described.

Proteins: CHEC-9 peptide, and functional variants thereof may be prepared in a variety of ways, according to known methods. The peptide may be synthesized using an automated peptide synthesizer. Alternatively, the peptide may be purified from appropriate sources, e.g., transformed bacterial or animal cultured cells or tissues, by immunoaffinity purification. The availability of nucleic acid molecules encoding CHEC-9 peptide enables production of the peptide using in vitro expression methods known in the art. For example, a CHEC-9 encoding polynucleotide may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or Gibco-BRL, Gaithersburg, Md.

Alternatively, larger quantities of CHEC-9 peptides may be produced by expression in a suitable prokaryotic or eukaryotic system. For example, part or all of a DNA molecule, such as a nucleic acid encoding CHEC-9 may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

The CHEC-9 peptide produced by gene expression in a recombinant prokaryotic or eukaryotic system may be purified according to methods known in the art. In a preferred embodiment, a commercially available expression/secretion system can be used, whereby the recombinant peptide/protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The human CHEC-9 peptide and functional homologs or variants thereof, prepared by the aforementioned methods, may be analyzed according to standard procedures. For example, such proteins may be subjected to amino acid sequence analysis, according to known methods. One such peptide variant which also has neuron protective activity is the peptide having the sequence CAHAQAESC.

The CHEC-9 peptide may be oxidized (cyclized), or akylated (lineraized).

Antibodies: The present invention also provides antibodies capable of immunospecifically binding to peptides of the invention. Polyclonal antibodies directed toward CHEC-9 peptide may be prepared according to standard methods. In a preferred embodiment, monoclonal antibodies are prepared, which react immunospecifically with CHEC-9 peptide.

Polyclonal and/or monoclonal antibodies may be prepared as described in several laboratory protocol handbooks, and scholarly journals including: Köhler and Milstein, Nature, 256: 495-7 (1975); Molecular Cloning: A Laboratory Manual, Sambrook et al. eds., Cold Spring Harbor Laboratory Press (1989); Ausubel et al. (supra), and Antibodies: A Laboratory Manual, Harlow and Lane eds., Cold Spring Harbor Laboratory Press (1988).

Polyclonal or monoclonal antibodies that immunospecifically interact with CHEC-9 peptide may be utilized for identifying and purifying CHEC-9 peptide. For example, antibodies may be utilized for affinity separation of peptides with which they immunospecifically interact. Antibodies may also be used to immunoprecipitate peptides from a sample containing a mixture of peptides/proteins and other biological molecules. Other uses of anti-CHEC-9 peptide antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

II. Uses of CHEC-9-Encoding Nucleic Acids, CHEC-9 Proteins and Antibodies Thereto CHEC-9-Encoding Nucleic Acids: CHEC-9-encoding nucleic acids may be used for a variety of purposes in accordance with the present invention. CHEC-9-encoding DNA, RNA, or fragments thereof may be used as probes to detect the presence of and/or expression of nucleic acids encoding CHEC-9 peptides. Methods in which CHEC-9-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR). Thus, CHEC-9-encoding nucleic acids of the present invention may be used for detecting CHEC-9 in vitro or in vivo.

Additionally, the nucleic acids of the invention may be used to identify genes encoding proteins that interact with CHEC-9 peptides (e.g., by the "interaction trap" technique).

The CHEC-9 nucleic acids of the invention may be introduced into host cells. In a preferred embodiment, mammalian cell lines are provided which comprise a CHEC-9-encoding nucleic acid or a variant thereof. Host cells contemplated for use include, but are not limited to NIH3T3, CHO, HELA, yeast, bacteria, insect and plant cells. The CHEC-9 encoding nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation and lipofection.

The host cells described above may be used as screening tools to identify compounds that modulate CHEC-9 expression and/or activity. Modulation of CHEC-9 expression and/or activity may be assessed by measuring alterations in CHEC-9 mRNA or peptide levels in the presence of the test compound.

As described above, CHEC-9-encoding nucleic acids are also used to advantage to produce large quantities of substantially pure CHEC-9 peptides, or selected portions thereof.

CHEC-9 Peptide: It has been discovered that CHEC-9 promotes survival of neural cells in vitro and in vivo, and inhibits phospholipase A2. Thus, peptide CHEC-9 and pharmaceutical preparations comprising the same have broad utility in the treatment of neuron damage, neurodegenerative disease, and disorders with an inflammatory component. The uses of these materials described hereinbelow are intended to exemplify their utility, and are not intended to limit the invention.

Such neurodegenerative diseases and disorders include, but are not limited to (1) trauma, (2) stroke, (3) nonspecific anoxia (i.e., anoxia due to drowning, suffocation, etc.), (4) neurodegenerative diseases such as Alzheimer's disease, Parkinson's disease and amyotrophic lateral sclerosis (ALS); and (5) mental retardation syndromes associated with progressive neuronal degeneration (e.g., cerebral palsies).

Disorders with an inflammatory component include, but are not limited to, (1) asthma; (2) autoimmune disorders; (3) allergies; (4) arthritis; and (5) any disorder which might benefit from treatment using a steroid or a phospholipase A2 inhibitor.

A pharmaceutical preparation of CHEC-9 is formulated for administration to patients by combining the peptide with a biologically acceptable medium, such as water, buffered saline, or osmotically-adjusted media such as polyol (e.g., glycerol, propylene glycol, liquid polyethylene glycol and the like) or suitable mixtures thereof. The term "biologically acceptable medium" includes all solvents, dispersion media and similar components which may be appropriate for the selected route of administration of the pharmaceutical preparation. The use of such biologically acceptable media for pharmaceutical preparations is well known in the art. Unless a conventional medium or agent is incompatible with the active ingredient of CHEC-9, its use in the pharmaceutical preparation of the invention is contemplated.

The pharmaceutical preparation is preferably administered parenterally, by introduction into the central nervous system of the patient. This may be accomplished by intracerebroventricular infusion targeted to the location of neuron damage. Other methods, such as systemic administration via an i.v. may also be utilized to administer a pharmaceutical preparation containing CHEC-9. Administration may be by any method that allows CHEC-9 to cross the blood/brain barrier, either alone or linked to a carrier, including injection into the bloodstream, subcutaneous or intramuscular injection, as well as oral, intranasal, rectal and ophthalmic administration. In a preferred embodiment, solutions comprising CHEC-9 may be injected subcutaneously.

CHEC-9 peptide may be administered topically or transdermally, such as in a cream, salve, spray, ointment, or dermal patch.

Alternatively, CHEC-9 peptides are incorporated into a solid matrix, which can be implanted into regions of the nervous system/brain requiring treatment. For example, a pre-determined concentration of CHEC-9 may be mixed in equal parts with a 2% sodium alginate medium, and entrapped in the resulting gel matrix. The sodium alginate gel is polymerized in the form of small beads by dropping the gel into a 0.5 M CaCl2 solution. Other solid or semi-solid biologically compatible matrices are also contemplated for use in the present invention. These include various natural biopolymers, such as xanthan and carob gums (See Mugnier et al., Appl. Environ. Microbiol., 50: 108-14 (1985).

The pharmaceutical preparation comprising CHEC-9 is advantageously formulated in dosage units, which is defined herein as a discrete unit of the pharmaceutical preparation appropriate for the patient undergoing treatment. As used herein, the term "patient" refers to humans and animals. A dosage will contain the quantity of active ingredient determined to produce the desired therapeutic effect in conjunction with the selected pharmaceutical carrier.

The appropriate dosage of a pharmaceutical preparation comprising CHEC-9 as the active ingredient may be determined by in vitro and in vivo procedures. The optimum effective concentration of CHEC-9 is dependent upon the type of neuron being treated and the protocol and source used for purification. Therefore, once the target neuron population has been identified, the optimum effective concentration of CHEC-9 may be determined by an in vitro assay. For example, a selected neuron population may be grown in culture for 2-4 days in defined serum-free medium. Pre-determined concentrations of CHEC-9 in an appropriate biological medium is then added to the culture dishes every 24 hours. After the incubation period, neurons and dendrites may be identified by immunocytochemically, e.g., with an antibody against a neuron-specific marker, such as MAP2. Neuron survival and neurite outgrowth is then determined. By comparing the effect of each concentration of CHEC-9 on neurite outgrowth and neuron survival, an optimum concentration for the specific neuron population is determined.

After the optimum in vitro concentration of CHEC-9 has been determined for a specific neuron population, an appropriate dosage may be deduced by an in vivo assay on laboratory animals, such as rats. An equivalent lesion in a primate or human would damage approximately 15-fold more cortical tissue. The area of brain damage is determined by standard imaging techniques, e.g., MRI. Therefore, that lesion cavity must be treated with an approximately 15-fold greater amount of the factor.

CHEC-9 may be administered in any effective dosage amount determined as set forth above. An exemplary dose is a subcutaneous administration of 50-500 µg/kg of CHEC-9 peptide. This dose may be administered immediately after, within 1 hour, 2 hours, 12 hours, or 1 day of acute injury, or periodically in the case of a chronic condition.

A pharmaceutical preparation containing CHEC-9 may be administered as a one-time dosage for cases of acute anoxia or trauma, or it may be administered at appropriate intervals in the case of chronic degenerative disease, until the symptoms of the disease are reduced or eliminated. The appropriate interval of administration of the pharmaceutical preparation will depend on the type of neuron damage being treated and the condition of the patient.

The CHEC-9 peptide of the invention may be administered in linear or cyclized form. Additionally, the CHEC-9 peptide of the invention may be administered in combination with another therapeutic agent, such as a steroid, a non-steroidal anti-inflammatory drug (NSAID), etc.

CHEC-9 Antibodies:

Purified CHEC-9 peptide, or fragments thereof, may be used to produce polyclonal or monoclonal antibodies which also may serve as sensitive detection reagents for the presence and accumulation of CHEC-9 peptide (or complexes containing CHEC-9 peptide) in mammalian cells or body fluids. Recombinant techniques enable expression of fusion proteins containing part or all of CHEC-9 peptide. The peptide may be used to advantage to generate an array of monoclonal antibodies specific for CHEC-9, thereby providing even greater sensitivity for detection of CHEC-9 in cells or body fluids.

Polyclonal or monoclonal antibodies immunologically specific for CHEC-9 peptide may be used in a variety of assays designed to detect and quantitate the peptide. Such assays include, but are not limited to: (1) flow cytometric analysis; (2) immunochemical detection/localization of CHEC-9 peptide; and (3) immunoblot analysis (e.g., dot blot, Western blot) of extracts from various cells. Additionally, as described above, anti-CHEC-9 antibodies can be used for purification of CHEC-9 peptide and any associated subunits (e.g., affinity column purification, immunoprecipitation).

Kits for Performing the Disclosed Methods:

In one broad aspect, the present invention encompasses kits for use in administering CHEC-9. Such a kit may comprise a CHEC-9 peptide in a pharmaceutically acceptable excipient, such as artificial cerebral spinal fluid. The kit may also comprise devices which facilitate administration of the peptide, such as catheters and syringes.

Further details regarding the practice of this invention are set forth in the following examples, which are provided for illustrative purposes only and are in no way intended to limit the invention. The following materials and methods are provided to facilitate the practice of the present invention.

EXAMPLE I

Survival of Neural Cells is Supported by CHEC-9

A thirty amino acid N-terminal fragment of DSEP called Y-P30, was originally purified from the culture medium of neural cell lines exposed to hydrogen peroxide. Y-P30 promotes neuron survival and inhibits the appearance and differentiation of monocyte derivatives (macrophages/microglia) in vitro and in vivo, including after systemic administration (Cunningham, T J et al., 1998; Cunningham, T. J., et al., 2000). The cDNA and the gene location for full length human DSEP have been identified and encode a 12 kD secreted polypeptide. When the full-length human protein is expressed in either mouse or human neural cells, these cells become resistant to a variety of toxic treatments, including immune cell attack in xenocultures and in vivo (Cunningham T J, et al., in press).

Based on the Y-P30 experiments, it was concluded that the survival and immune evasion activities of DSEP could be accomplished for the most part by the N terminal 30 amino acids. However, the sequence of the secreted form of the native peptide differs from Y-P30 in that the latter was made with cysteines at both positions 15 and 23 while the native molecule contains only one cysteine at position 15 (with a lysine at position 23). In ongoing studies of biologically active forms of Y-P30, it was found that crosslinking the cysteines confers greater survival-promoting activity in vitro than a similar 30 amino acid fragment made without the K to C substitution, or a scrambled peptide where the amino acids (including those between the two cysteines) were out of order. The K to C substitution therefore stabilizes an active conformation of DSEP by allowing the formation of an intramolecular disulphide bond. Therefore this part of the Y-P30 sequence—CHEASAAQC, designated herein as CHEC-9, was tested for DSEP/Y-P30-like activity.

Synthesis of Peptides.

Peptide synthesis was performed at the Protein Chemistry Laboratory in the Department of Pathology and Laboratory Medicine University of Pennsylvania. The peptides were HPLC purified on a C18 column, dried, reconstituted in water and dried again. Peptide stock solutions (200-250 µg/ml, 218-273 µM) were prepared in 50 mM tris pH=7.4 or DMEM and incubated at room temperature overnight or for 2 hrs at 37°. Free sulphydryls were measured using Ellman's reagent (DTNB, 0.04 mg/ml) in 0.1M $NaH_2PO_4$, 20 mM EDTA, pH=8 by mixing 25 µl sample with 275 µl reaction buffer. Absorbance of these samples was measured at 450 nm with a 808-xl microplate reader (Biotek Instruments), and was at background levels after cross-linking. In addition, the formation of intramolecular disulphide bond in selected samples was verified by determining the exact molecular mass of the unfolded versus folded peptides using electrospray mass spectrometry (LC-ZQ Mass Spectrometer, Waters)

CHEC-9 Protects Neural Cells Subjected to Stress In Vitro

Various concentrations of CHEC-9 were tested in a stress test consisting of medium change followed by serum deprivation (see Cunningham, et al., 2000, 2002). The CHEC-9 molecule was found to rescue cells when used at concentrations of 0.1 and 0.01 µM (10-100 picomolar). Optimal activity of the peptide was achieved after pre-incubation (250 nM) with 10 mM adenosine triphosphate (Na-ATP) in a reaction mixture containing 120 mM KCl, 1 mM $CaCl_2$, 25 mM NaCl, and 25 mM tris (pH=7.4). This mixture was diluted in culture medium and then added to the stressed cells at the appropriate active picomolar concentrations. Vehicle treatment consisted of incubation buffer without the peptide at the appropriate dilutions. Cell survival is measured by either counting surviving attached cells or, as shown in FIG. 1, by colormetric determination after applying an electrocoupling reagent that responds to chemical reactions in normal cellular respiration. The number of neurons protected in the cultures is estimated to be between 3 and 10 fold, depending on the length of serum deprivation and the starting concentration of cells.

CHEC-9 Protects Cerebral Cortex Neurons after Cortical Stab Wounds in Rats

Figure 2:
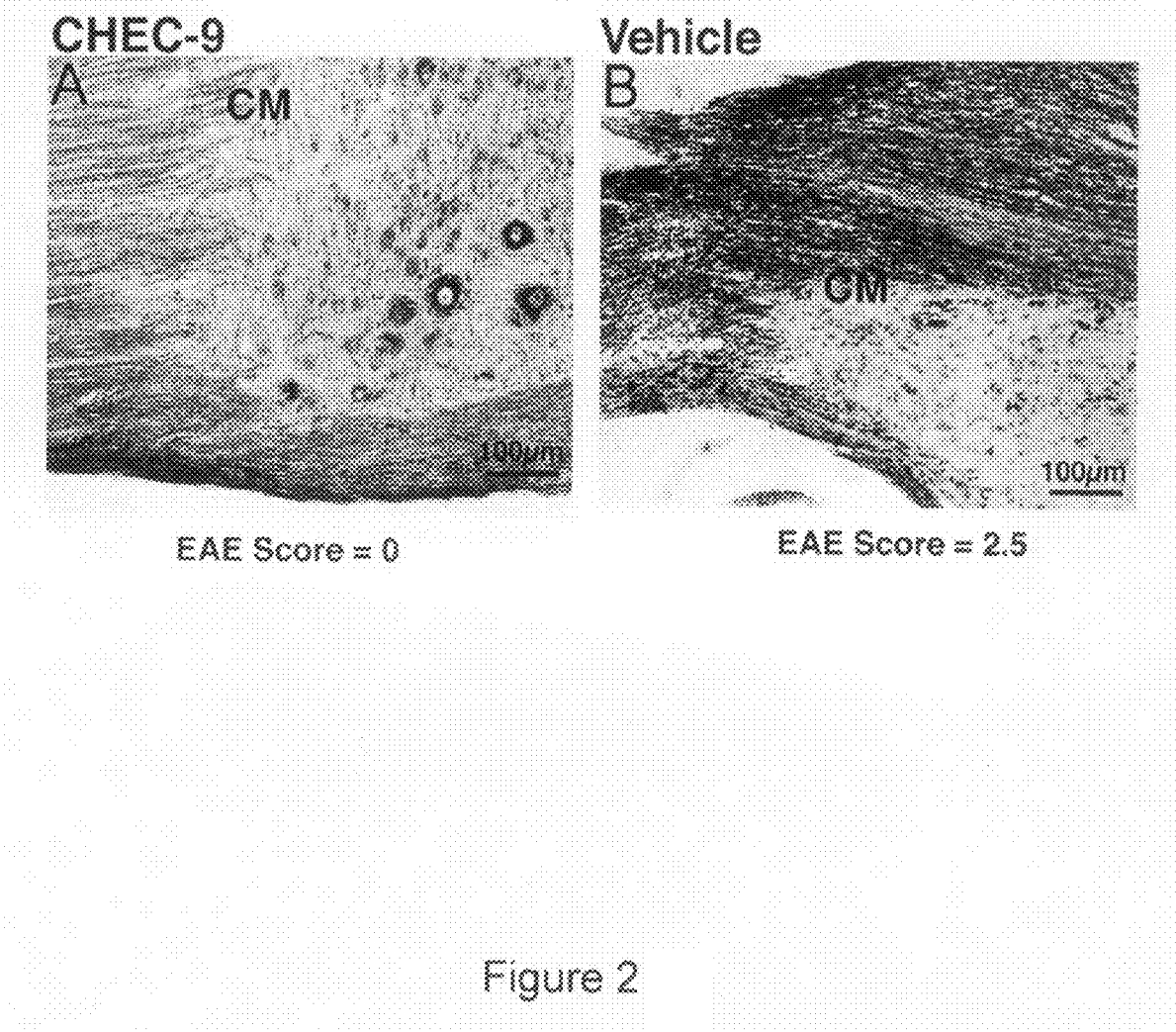
FIG. 2 shows the coronal section through the cerebral cortex of rats that received stab wounds in area 3. The rats survived for 4 days following the lesion after which their brains were processed for cresyl violet staining or immunostaining with macrophage/microglia marker ED-1 in adjacent sections (inset). The vehicle treated animal shows a typical response to the lesion including a pronounced invasion of inflammatory cells and degeneration of cortical tissue. Systemic treatment with CHEC-9 inhibits both processes. Bar=1 mm.

Stab wounds were administered to the rostral cortical area 3 of the exposed cerebral cortex (with dura intact) of rats, using a dissecting knife (blade=1×2 mm). The wound typically produces a significant local inflammatory response, disruption of the functional layers of the cortex, and marked atrophy and degeneration of neurons (FIG. 2, left panel). The principal immune cells involved in the inflammatory response are macrophages and microglia (FIG. 2, inset). Subcutaneous injection of CHEC-9 (0.4 mg/Kg bilaterally in the skin of the shoulder), 20 min after the placing of the wound, results in a significant anatomical sparing of the perilesion parenchyma, as well as a more restricted inflammatory response (FIG. 2, right panel).

Activation of Microglia Cells is Inhibited by CHEC-9

Figure 3:
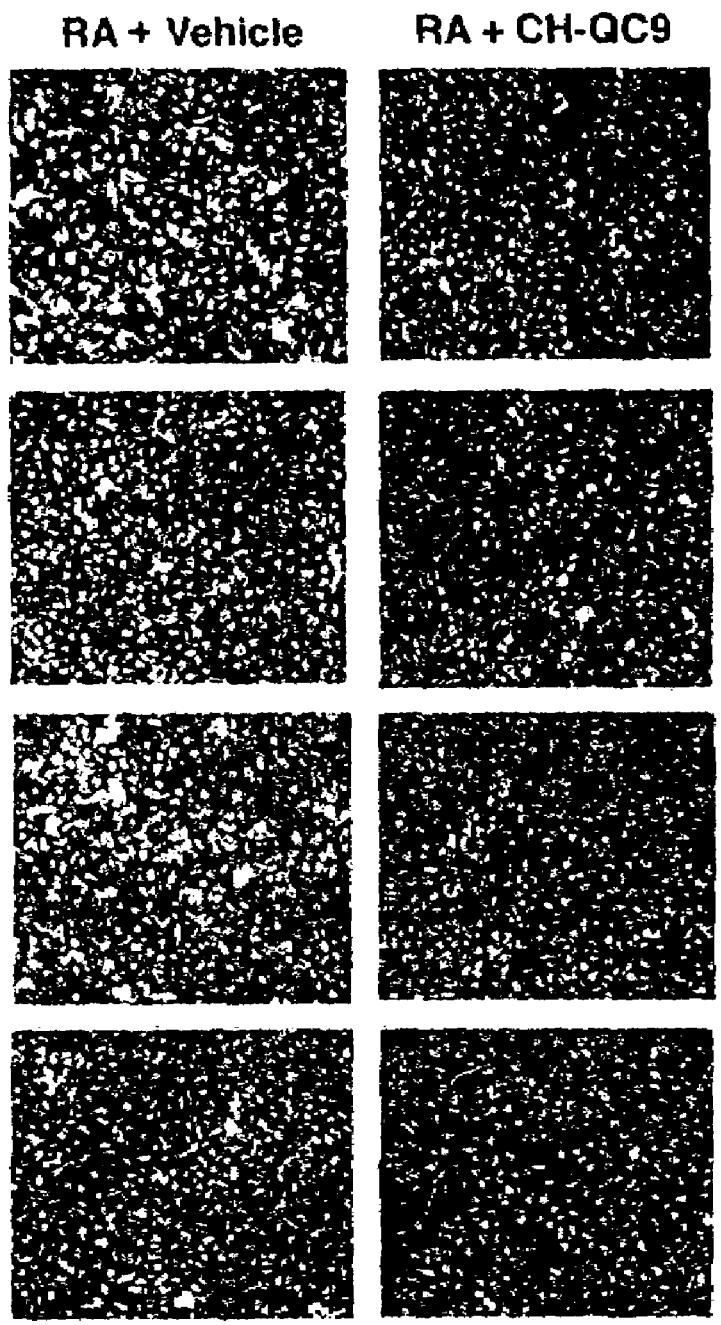
FIG. 3 shows microglia cells which were purified from neonatal rats, activated with 100 nM retinoic acid (RA) on days 1 and 2 in vitro, and examined on day 3 or 4. It is shown that TNFα immunoactivity is reduced in these cells that were treated with 1 nM CHEC-9 during the period of RA activation.
Figure 4:
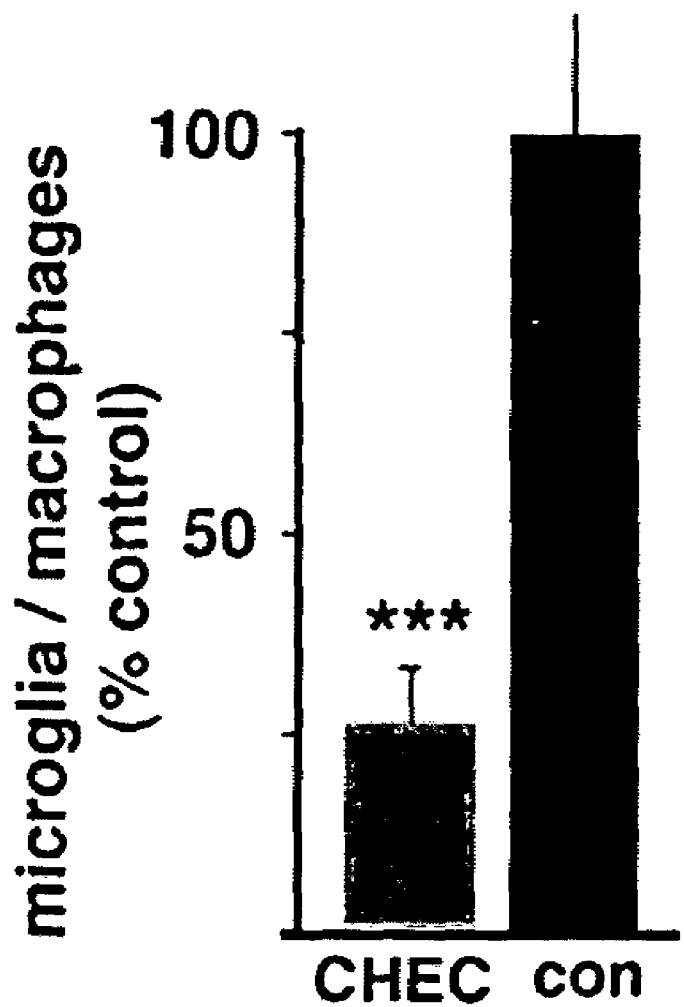
FIG. 4 is a graph showing that percent concentrations of microglia/macrophages at the dorsal and ventral margins of the lesions 4 days after stab wounds to the parietal cortex of rats, are lower in animals which were administered the CHEC-9 peptide. Near marginal or white matter layers, where ameboid cells appeared most consistently in both groups, the number was reduced by 75% (N=6 in each group, p=4×10−3). Such cells are very sparse in the midportions of the lesions after peptide treatment.

Microglia cells were purified from neonatal rats according to established procedures and allowed to develop for an additional 72-96 hrs in vitro, after which the cells are found to be 90-98% ED-1+. ED-1 is a marker specific for rat microglia. Contaminating cells are GFAF+ (suggesting they are astrocytes) or unreactive. TNFα immunoreactivity is at moderate to low levels in these cultures. If, however, the cells are activated with 100 nM retinoic acid on days 1 and 2 in vitro and examined on day 3 or 4, the ED-1 positive microglia cells display rounded morphology with small or blunt processes suggesting that the cells are transformed into amoeboid microglia. (sometimes referred to as brain macrophages, Milligan, et al 1991a;b). TNFα immunoreactivity is more intense in these cultures. These same morphological changes have been described in several studies of microglial activation in vitro (e.g., Siao and Tsirka, 2002; Bothatschek, 2001). When the microglia are treated with 1 nM CHEC-9 during the period of activation by RA (30 min after the RA treatment), the cells in the CHEC-9 treated cultures are on average smaller with distinct processes suggesting the transformation to the activated amoeboid morphology is inhibited (data not shown). Likewise, TNFα immunostaining in the cells is reduced. An experiment with eight RA treated cultures is shown in FIG. 3. The 4 cultures in the right panels were also treated with 1 nM CHEC-9 peptide.

CHEC-9 Protects Neural Cells and Inhibits Inflammation

Animals, Surgery, and Histology.

All animal procedures were in compliance with the relevant laws and institutional guidelines, and were approved by Animal Care and Use Committeee of Drexel University College of Medicine. The lesion studies were conducted on 15 long evans hooded rats weighing 225-275 g. Twelve of these rats were deeply anesthetized with ketamine/xylazine and placed in a sterotaxic holder. A 4×2 mm (rostrocaudal×mediolateral) skull opening was made on the right side starting just behind the coronal suture and centered at a mediolateral position of +2.5 mm relative to bregma. A dissecting knife was penetrated through the dura and cortex in the center of this skull opening to a depth of 1 mm. The skull defect was filled with bone wax, the skin sutured closed, and the animal placed on a heating pad. Twenty minutes later, 0.4 cc of solution containing 100 µg of peptide (~0.4 mg/kg, 6 rats) or DMEM vehicle (6 rats) was injected under the skin of the shoulder near the midline. The rats were perfused 4 days later and their brains processed for histology and immunohistochemistry as in previous studies. Three rats were sacrificed without surgery or treatment. Alternate coronal sections of these brains were stained with cresyl violet acetate and immunostained with the TUJ1 antibody to neuronal specific tublin, isotype III (Covance Research Products) or monocyte marker ED-1 Serotec. Secondary antibodies were FITC or Rhodamine conjugated (Jackson Immunolabs). The density of ED-1+ ameboid microglia in the perilesion parencyma wound was calculated after experimentally blinded counting of 4 fields (dorsal and ventral margins of the wound) in 2 sections through the lesion.

Discussion

Four days following perfusion, there were no obvious behavioral differences between the treated and untreated groups. Both displayed normal locomotor activity and were alert and responsive to orienting stimuli. Cresyl violet-stained sections through the brains of control rats revealed pronounced neuronal degeneration and accumulation of large numbers inflammatory cells in the wound and in the parenchyma surrounding the wound. Immunostaining with the cell specific marker ED-1 showed that many of these cells were macrophages and microglia. The microglia were activated and thus predominantly of the round ameboid type. The cortical layers that are usually obvious in somatosensory area 2 (where the laminae are distinctive) were no longer apparent because of the invasion of these normeuronal cells, and because of the frank degeneration of the neurons. In rats injected with CHEC-9 both the disruption of the cerebral cortex and accumulation of inflammatory cells in the parechyma was inhibited. This effect was striking and apparent in all the rats treated with the peptide. The most obvious difference found after CHEC-9 treatment was the sparing of the cortical tissue adjacent to the wound in area 2. Granular and pyramidal neurons appeared of near normal size and distribution, and as a result, the cortical layers also appeared normal. In addition, rounded ED-1 positive cells were significantly reduced in the cortex. There were ED-1 reactive profiles scattered in the tissue near the lesion after CHEC-9 treatment, but the vast majority of these appeared to be processes of small, ramified cells, which is the morphology of nonactivated or "resting" microglia.

EXAMPLE II

CHEC-9 is a Potent Phospholipase A2 Inhibitor, and Also Inhibits Paltelet Aggregation Measurement of PLA2, Platelet Activity.

Trunk blood was collected from 16 additional Long Evans and Sprague Dawley rats of both sexes following decapitation. Fourteen of these rats were paired according to strain, sex, and weight and injected with a control peptide/vehicle or with CHEC-9 forty-five minutes prior to sacrifice. Phospholipase A2 activity was determined in 10 rats and platelets were isolated from the remaining 6 animals.

Serum samples and purified bee venom phospholipase were tested for PLA2 activity using a 1,2-bis(heptanoylthio) glycerophosphocholine substrate (Caymen Chemical) which produces a DTNB reactive sulfhydryl upon cleavage of phospholipids at the at the sn-2 position (target of all PLA2 enzymes). DTNB reactivity with serum, peptides, or PLA2 at the concentrations used in these experiments was not detectable in the absence of substrate (or vice versa). This substrate is sometimes preferred for inhibitor studies since with more natural substrates there is the possibility for interfacial disruptions rather than true inhibition (Mihelich E D, et al., 1997). All reactions were conducted in triplicate or quadruplicate in microwells at 25° with substrate concentrations of 50-500 µM. The measurements were made on an ELX 808 reader (Biotek Instruments) programmable for kinetic studies, and further analysis was performed using nonlinear regression software from Graphpad which fit the data to a hyperbola (one site binding) for determining Vmax and Kd. For experiments with bee venom, CHEC-9, control peptides or tris solvent was mixed with equimolar sPLA2 and incubated at 37° for 30 min. Platelets were isolated from whole blood treated with 1.5 mM EDTA after gradient centrifugation in a 22:5 mixture of Tris glycine buffer and 60% iodixanol (OptiPrep, Axis Sheild). The platelets were washed twice in Hanks balanced salt solution. Peptide was added in the second wash if the animal was untreated, and after an additional 20 min, the medium was collected and dialyzed overnight. Rates of aggregation of the platelets were then determined in response to indicated concentrations of PMA in HBSS by the method of Bednar, et al, (1995) in which the absolute value of the rate of change of $A_{650}$ is proportional to rate of aggregation. The dialyzed supernatants were dried resuspended in SDS sample buffer and electrophoresced under reducing and non reducing conditions. Western blots were prepared as in previous studies using a polyclonal antibody to sPLA2 IIa (Caymen Chemical) that is reactive with rats platelet PLA2. Nonparametric statistical analysis (Mann Whitney) was used throughout the study.

Discussion

Figures 5A, 5B, 5C, 5D:
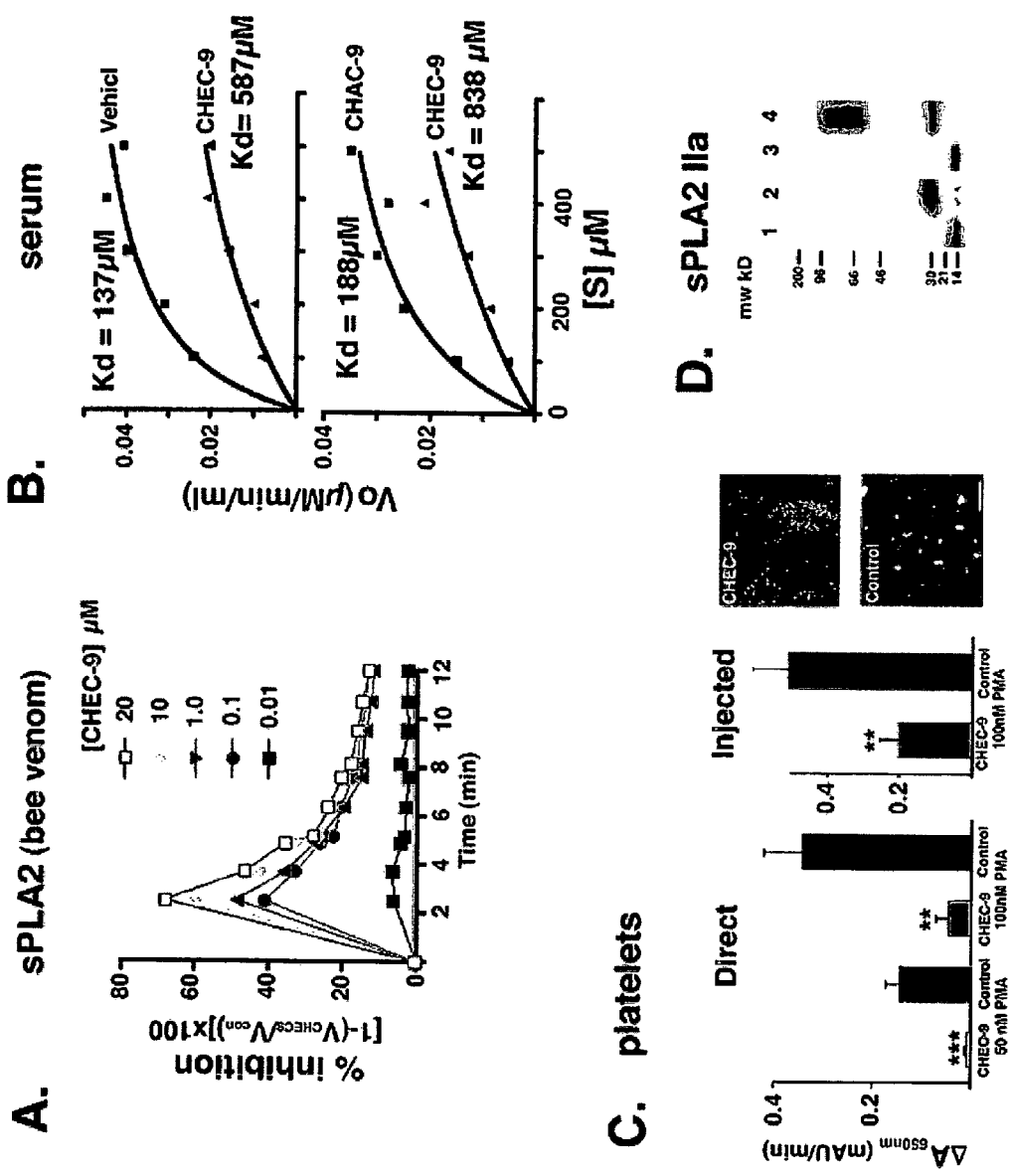
FIGS. 5A-D show that CHEC-9 treatment inhibits PLA2 enzyme and related activities. (A). CHEC-9 inhibition of phospholipase A2 from bee venom is maximal within the first 2 min of the reaction at a variety of peptide concentrations. (B). Representative Michaelis-Menton Plots plot using 5% serum samples from CHEC-9 and control-injected rats. The bottom plot is from a pair of rats in which one was injected with CHEC-9 and one with a peptide where the positions of glutamate and adjacent alanine were switched (CHAC-9). The dissociation constants are noted on the plots. (C). CHEC-9 treatment inhibits platelet aggregation. Platelets were isolated from untreated rats and incubated with 0.1 nM CHEC-9 or equivalent tris solvent in HBSS (left graph), or from rats treated with 100 µg CHEC-9 or vehicle (right graph). Rates of aggregation were determined over a period 5-30 minutes after addition of the indicated concentrations of PMA (p<0.01, *p<0.001. n=10 each in 2 direct treatment and 2 injection experiments). Micrographs of CHEC-9 and control treated platelets at the end of one of the experiments are shown. Bar=100 µm. (D). CHEC-9 treatment results in a typical migration of platelet sPLA2 IIa on SDS gels. Isolation and washing of platelets prior to above analysis caused release of sPLA2 IIa which migrates, as expected, with an apparent molecular weight of ~14 kD on SDS gels run under reducing conditions (lanes 1,3 control, treated). SPLA2 released from platelets treated with CHEC-9 either 100 µg injected into the animal, (lane 2), or added directly (0.1 nM) to platelets isolated from untreated rats (lane 4) shows strong sPLA2 IIa bands that run with higher apparent molecular weights. This suggests that treatment had modified the sPLA2 IIa enzyme structure and/or promoted the formation of stabilized enzyme complexes or aggregates.

Once its survival-promoting properties were recognized, CHEC-9 was screened in several enzymatic and nonenzymatic assays related to cell survival and immunomodulation. In one of these, the peptide was found to inhibit activity of a secreted phospholipase A2 (sPLA2) derived from bee venom. In these experiments, 70 nM of bee venom sPLA2 was reacted with 50 µM of a glycerophosphocholine substrate in the presence of various concentrations of CHEC-9 (FIG. 5A). The velocity of the reaction was measured and found to be reduced significantly by CHEC-9 at concentrations of 100 nM and above. Next, the PLA2 enzyme activity of serum from peptide and control-injected rats was compared in this same assay after treating the rats according to the regimen used in the lesion studies. Rat serum shows significant phopholipase A2 activity that appears to follow Michaelis-Menten kinetics, at least in the range of serum and substrate concentrations used in these experiments. There was inhibition of the serum PLA2 activity in rats injected with CHEC-9. FIG. 5B shows representative Michaelis-Menten plots using peptide-treated and control sera, including serum of rats treated with a scrambled version of the CHEC-9 peptide. In the latter experiments, it was found that simply inverting the order of the glutamate and the alanine (that is E3-A4 to A3-E4) was sufficient to eliminate the inhibitory activity of CHEC-9. Analysis of kinetic plots from CHEC-9-treated and control rats showed that the peptide, on average, reduced the maximum velocity of the reaction, however this effect was variable and not statistically significant (Vmax CHEC-9=70.3+7.4%, of controls, p=0.132 n=6). The Kd of the reaction was increased in all peptide treated rats, as much as 6-fold, and the difference between peptide and control-treated rats was very significant (Kd CHEC-9=313%+68% of controls, p=0.0087, n=6). These experiments provide evidence that the basis for the peptide's inhibition of PLA2 activity in serum is a reduction in the affinity of the enzyme(s) for substrate after treatment.

Platelet activation is a PLA2-related activity and is also affected by CHEC-9 treatment. When platelets are isolated from the blood and then washed, they become activated and begin to aggregate spontaneously. It was observed that this spontaneous aggregation was inhibited by prior treatment with CHEC-9, either using platelets from peptide-injected rats or after direct treatment of isolated platelets with 0.1 nM CHEC-9 (data not shown). If the platelets are then treated with phorbol-12-myristate-13-acetate (PMA) and agitated, platelet aggregation proceds at a brisk rate for at least the next 5-30 min, and can be monitored spectrophotometrically.

This response is also inhibited for platelets treated with CHEC-9 directly or by injections into rats prior to isolation (FIG. 5C). PMA is suggested to induce platelet activation in concert with mobilization of intracellular calcium by stimulating phosphorylation of cytosolic PLA2 (McNicol A, et al., 1998). It is therefore possible that the peptide effects cytoplasmic PLA2 directly, or indirectly through inhibition of secreted PLA2 enzymes which are released from activated platelets (Han W K, et al., 2003; Balboa M A, et al., 2003).

While there are likely to be several PLA2 isoforms present in serum, rat platelet sPLA2 (sPLA2 IIa) appears to be abundant in rat serum (Mihelich E D, et al., 1997; Hayakawa M, et al. 1987). The release of sPLA2 (IIa) from washed platelets was confirmed by Western blots of platelet supernatants. Interestingly, the sPLA (IIa) released by platelets treated with CHEC-9 (either in the rat or in vitro) produced a typical bands on Western blots, migrating in SDS gels (under reducing conditions) with apparent molecular weights greater than the expected 14 kD (FIG. 5D). The most prominent sPLA2 immunoreactive bands after CHEC-9 treatment migrated above 40 kD, while control rats always showed a 14 kD band, and rarely showed higher molecular weight species. The final position of the sPLA2 bands after CHEC-9 treatment was variable from sample to sample. However, the expected 14 kD species was not observed in CHEC-9 peptide-treated samples, suggesting that treatment had modified the enzyme structure and/or promoted the formation of stabilized enzyme complexes or aggregates. Such aggregates might have a lower affinity for substrate which would explain the kinetic differences in PLA2 reactions found in peptide-treated rats.

Fatty acids, phospholipids, and other lipid mediators of inflammation are increased following brain damage and in neurodegenerative diseases, and much of this increase results from phospholipase A2 activity (Lipton P., 1999; Bazan N G, et al., 2002; Lukiw W J, et al., 2000). These products of lipid metabolism, along with the coordinated activity of cytokines and other mediators, contribute significantly to inflammation, and therefore also contribute significantly to neuron death, either that which is observed after acute lesions to the CNS, or that found in many progressive neurodegenerative diseases. In addition, there are numerous examples of cross talk between lipid and cytokine mediated inflammatory responses that may amplify these responses especially in the early stages of inflammation (Thommesen L, et al., 1998; Beck S, et al., 2003). Finally, the breakdown of phospholipids by PLA2 enzymes produces major changes in membrane function and signaling properties, and leads to increases in free fatty acid production and therefore free radical formation. All these changes are also potentially damaging to neurons and most other cell types.

These experiments indicate that CHEC-9 is effective to treat both acute and chronic neurodegenerative and inflammatory conditions. The peptide's effects on other participants in PLA2-arachidonic acid pathway may prove interesting because many of these are the targets of potential drug therapies for inflammatory disorders in and outside the nervous system. On the other hand, one advantage of upstream inhibition of PLA2, presumably also an advantage for corticosteroids, is that upstream inhibition eliminates the contribution of downstream functionally redundant products or other participants in PLA2-directed metabolism, which may overcome the effects of drugs targeted downstream to more specific elements in these pathways.

EXAMPLE III

Anti-Y-P30 Antibody Produces Increase in Cortical Lesion Size and Sera Toxicity

This example demonstrates that there is a DSEP-like polypeptide in the rat brain that cross-reacts with affinity-purified polyclonal anti-human DSEP antibodies (FIG. 6). Rats were immunized with the N terminal peptide of human DSEP (Y-P30) conjugated to Keyhole Limpet Hemocyanin (KLH). Reactivity of their sera to DSEP was confirmed by Western blots and ELISA. Small cortical lesions were produced in the immunized rats. When the rats were sacrificed the extent of damage from the lesion, and the response of macrophages/microglia was tested. Additionally, rat antiserum was tested in a cell viability assay. It was found that DSEP immunized rats have exaggerated cortical lesions and increased cytotoxicity of their sera.

Immunizations, Surgery, Adverse Reactions.

Injections and boosts were subcutaneous, bilaterally in the shoulder over a period of 1.5 months. Control rats were immunized against KLH only. Serum titers of DSEP specific antibodies were measured by ELISA. At the time of sacrifice, titers of the rats used in this study were at least 1:1000 measured in multiple samples (data not shown). In addition, when DSEP antisera were tested in a cell killing assay they were found to be consistently more effective than KLH antisera (see below). Data was collected from 36 rats, 30 of which had small lesions of cortical area 2 near the area 2/3 border. The lesion is produced by stereotaxic positioning of a guide, opening the dura, and placing a 1 $mm^3$ piece of gelfoam on the cortical surface with light pressure. Fifteen of these rats were immunized against DSEP-KLH and 15 against KLH alone. Nine rats from each group were sacrificed 7 days after surgery and 6 were sacrificed after 4 days. Four immunized rats (2 from each group) were sacrificed without surgery and two rats were normal. There were no apparent adverse reactions to the immunizations in either group. Gross behavior of all rats was similar. There was no evidence of increased inflammatory reactions peripherally or, after sacrifice, in the CNS of immunized rats without surgery.

Lesion Volumes and ED1 Immunoreactivity

Figures 6A, 6B, 6C:
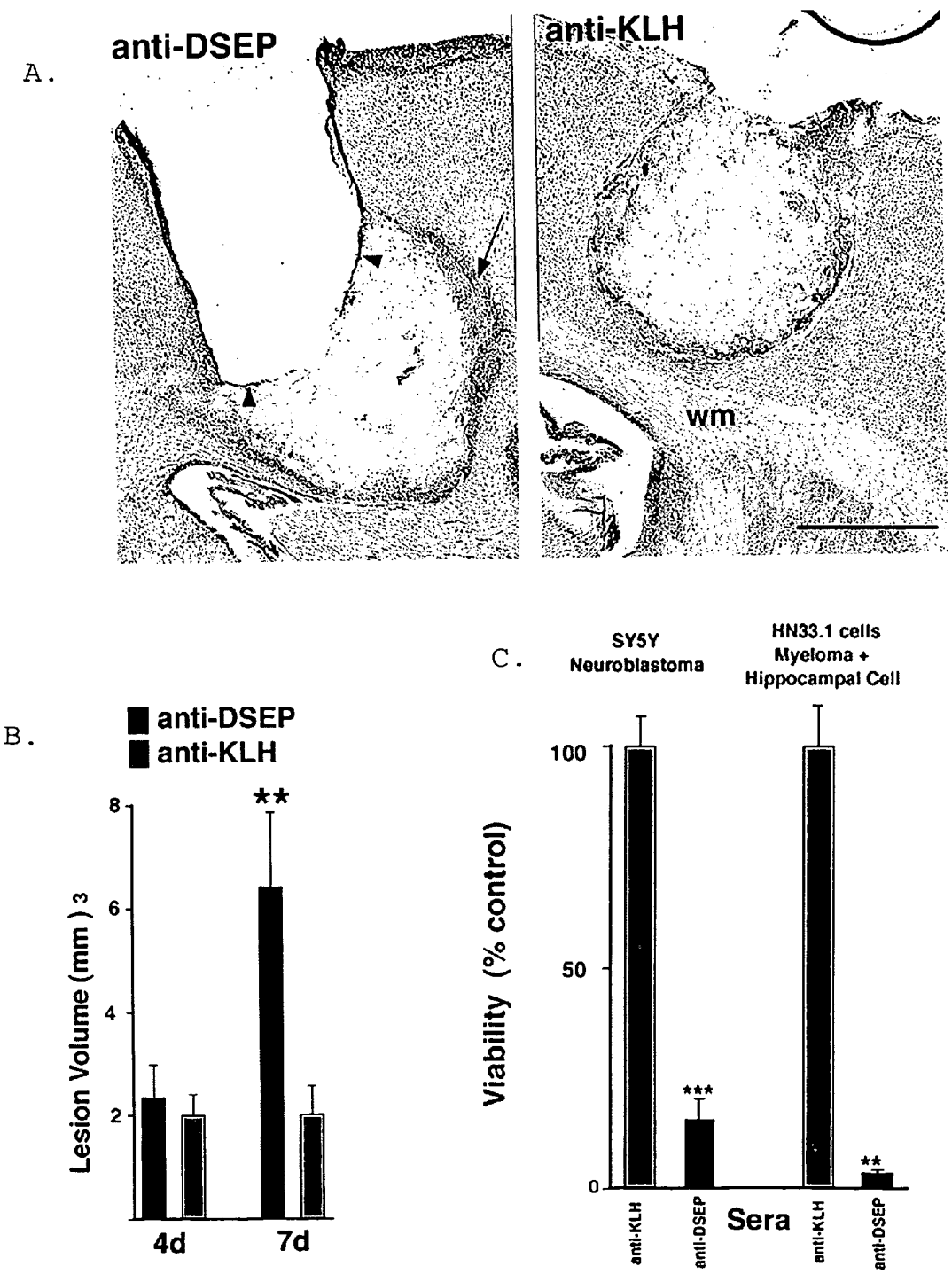
FIGS. 6A-C show that anti-YP30 antibody produces increased cortical lesion size and sera toxicity. (A) Coronal sections through medial part of cerebral cortex seven days after a lesion in area 2 of rats immunized against DSEP-KLH or KLH carrier protein. The lesions are made by placing a 1 mm$^3$ piece of gelfoam on the cortical surface. There are accumulations of cells at the margins of the lesions (large arrow and arrowheads) many of which are microglia/macrophages. At the 7 day survival, the lesions are considerably larger in rats immunized against DSEP, as can be seen in the photomicrographs and graph of volume measurements from serial sections (p<0.001 at 7 days, n=9; n.s.d at 4 days, n=6; A, B). Note also that the lesion in the anti-DSEP rat appears to have expanded from the original boundaries (arrowheads) into the adjacent parenchyma and white matter leaving behind a large cyst. Bar=1 mm. (C) Graph showing killing of SY5Y and HN33.1 cells by DSEP antisera. The cells were treated with 5% serum from rats immunized against DSEP-KLH conjugate or KLH alone (protein concentrations were equivalent). Viability was measured with the WST electrocoupling reagent 72 hrs after treatment and expressed as a percentage of the control value (anti-KLH). Cells treated with DSEP antisera degenerate while those treated with anti-KLH do not.

Four and 7 days following surgery, lesion volumes in anti-KLH rats were in a range that was consistent with parallel studies. The differences in lesion sizes were not statistically significant in rats surviving for 4 days (FIG. 6B). However at 7 days following surgery, lesion volumes in rats immunized against DSEP were more than 3-fold larger (FIGS. 6A, 6B). The macrophage/microglial response to these lesions was examined after 7 days. As might be expected because of the larger lesions, the anti-DSEP rats had an exaggerated appearance of ED1+ cells at the margins of the lesion and in surviving deep white matter tracts surrounding the lesion (not shown).

Cell Viability Assay.

The antisera from rats immunized with DSEP-KLH were cytotoxic to both HN33.1 and SY5Y cells. Anti-sera from 10 out of the 15 rats in each group was tested at a 1:20 dilution. In all cases, the anti-DSEP sera were clearly more toxic to the cells than the control sera (FIG. 6C). During the first 24 hrs following treatment, sera from both groups caused an apparent injury response and scattered degenerated cells, possibly due to complement-mediated mechanisms. Heating the sera for 30 or 60 min at 55° to destroy complement had variable effects on the cultures but tended to improve this initial response. By 48-72 hrs the cells treated with anti-KLH sera had mostly recovered while the cells treated with the anti-DSEP were degenerated completely.

REFERENCES

Balboa M A, Perez R, Balsinde J. (2003) Amplification mechanisms of inflammation: Paracrine stimulation of arachidonic acid mobilization by secreted phospholipase A2 is regulated by cytosolic phospholipase A2-derived hydroperoxyeicosatetraenoic acid. J Immunol 989-994.

Barone F C, Arvin B, White R F, Miller A, Webb C L, Willette R N, Lysko P G, Feuerstein G Z. (1997). Tumor necrosis factor-alpha. A mediator of focal ischemic brain injury. Stroke 28:1233-1244.

Bazan N G, Colangelo V, Lukiw W J. (2002) Prostaglandins and other lipid mediators in Alzheimer's disease. Prostaglandins Other Lipid Mediat 68-69:197-201.

Beck S, Lambeau G, Scholz-Pedretti K, Gelb M H, Janssen M J W, Edwards S H, Wilton D C, Pfeilschifter J, Kaszkin M. (2003) Potentiation of tumor necrosis factor a-induced secreted phospholipase A2 (sPLA2)-IIA expression in mesangial cells by an autocrine loop involving sPLA2 and peroxisome proliferator-activated receptor a activation. J Biol Chem 278:29799-29812.

Bohatschek M, Kloss C U A, Kalla R, Raivich G. (2001). In vitro model of microglial deramification: ramified microglia transform into amoeboid phagocytes following addition of brain cell membranes to microglia-astrocyte cultures. J Neurosci Res 64:508-522.

Cunningham T J, Jing H, Akerblom I, Morgan R, Fisher T S, Neveu M. Identification of the human cDNA for new survival/evasion peptide (DSEP): Studies in vitro and in vivo of overexpression by neural cells. Exp Neurol (in press).

Cunningham T J, Jing H, Akerblom I, Morgan R, Fisher T S, Neveu M. (2002). Identification of human cDNA for new survival/evasion peptide (DSEP): Studies in vitro and in vivo of overexpression by neural cells. Exp Neurol 177:32-39.

Cunningham T J, Jing H, Wang Y, Hodge L. (2000). Calreticulin binding and other biological activities of survival peptide Y-P30 including effects of systemic treatment of rats. Exp. Neurol 163:457-468.

Cunningham, T J, Hodge l, Speicher D, Reim D, Tyler-Polz C, Levitt P, Eagleson, K, Kennedy S, Wang Y (1998) Identification of a survival-promoting peptide in medium conditioned by oxidatively stressed cell lines of nervous system origin. J Neurosci 18:7047-7060.

Flower R J, Blackwell G J. (1979) Anti-inflammatory steroids induce biosynthesis of a phospholipase A2 inhibitor which prevents prostaglandin generation. Nature 278:456-459.

Farooqui A A, Litsky M L, Farooqui T, Horrocks L A. (1999) Inhibitors of intracellular phospholipase A2 activity: their neurochemical effects and therapeutical importance for neurological disorders. Brain Res Bull. 49:139-153.

Han W K, Sapirstein A, Hung C C, Alessandrini A, Bonventre J V. (2003) Cross-talk between cytosolic phospholipase A2 alpha (cPLA2alpha) and secretory phospholipase A2 (sPLA2) in hydrogen peroxide-induced arachidonic acid release in murine mesangial cells: sPLA2 regulates cPLA2 alpha activity that is responsible for arachidonic acid release. J Biol. Chem. 278:24153-24163.

Hayakawa M, Horigome K, Kudo I, Tomita M, Nojima S, Inoue K. (1987) Amino acid composition and NH2-terminal amino acid sequence of rat platelet secretory phospholipase A2. J biochem 101:1311-1314.

Hull M, Lieb K, Fiebich B L. (2002) Pathways of inflammatory activation in Alzheimer's disease: potential targets for disease modifying drugs. Curr Med Chem 9:83-88.

Jander S, Schroeter M, D'Urso D, Gillen C, Witte O W, Stoll G. (1998). Focal ischaemia of the rat brain elicits an unusual inflammatory response: early appearance of CD8+ macrophages/microglia. Eur J Neurosci 10:680-688.

Lavine S D, Hofman F M, Zlokovic B V. (1998). Circulating antibody against tumor necrosis factor-alpha protects rat brain from reperfusion injury. J Cereb Blood Flow Metab 18:52-58.

Lukiw W J, Bazan N G. (2000) Neuroinflammatory signaling upregulation in Alzheimer's disease. Neurochem Res. 25:1173-1184.

Lipton P. (1999) Ischemic cell death in brain neurons. Physiol. Rev. 79:1431-568.

McNicol A, Shibou T S. (1998) Translocation and phosphorylation of cytosolic phospholipase A2 in activated platelets. Thromb Res 92:19-26.

Mihelich E D, Carlson D G, Fox N, Song M, Schevitz R W, Snyder D W. (1997) Structure-based design and therapeutic potential of phospholipase A(2) inhibitors. Prog Surgery 24:140-145.

Milligan C E, Cunningham T i, Levitt P. (1991a). Differential immunochemical markers reveal the normal distribution of brain macrophages and microglia in the developing rat brain. J Comp Neurol 314:125-135.

Milligan C E, Levitt P, Cunningham T J. (1991b). Brain macrophages and microglia respond differently to lesions of the developing and adult visual system. J Comp Neurol 314: 136-146.

Rothwell N J, Luheshi G, Toulmond S. (1996) Cytokines and their receptors in the central nervous system: physiology, pharmacology and pathology. Pharmacol Ther 69:85-95.

Siao C J, Tsirka S E. (2002). Tissue plasminogen activator mediates microglial activation via its finger domain through annexin II. J Neurosci 22:3,353-3358.

Stoll G, Jander S, Schroetor M. (1998). Inflammation and glial responses in ischemic brain lesions. Prog Neurobiol 56:149-171.

Thommesen L, Sjursen W, Gasvik K, Hanssen W, Brekke O L, Skattebol L, Holmeide A K, Espevik T, Johansen B, Laegreid A. (1998) Selective inhibitors of cytosolic or secretory phospholipase A2 block TNF-induced activation of transcription factor nuclear factor-kappa B and expression of ICAM-1. J Immunol 161:3421-3430.

Turrin N P, Gayle D, llyin:S E, Flynn M C, Langhans W, Schwartz G J, Plata-Salaman C R. (2001). Pro-inflammatory and anti-inflammatory cytokine mRNA induction in the periphery and brain following intraperitoneal administration of bacterial lipopolysaccharide.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated peptide consisting of the sequence of CHEASAAQC (SEQ ID NO.: 1).

2. A pharmaceutical preparation comprising the isolated peptide of claim 1, in a biologically acceptable carrier.

3. A kit comprising:
a) an isolated peptide consisting of the sequence of CHEASAAQC (SEQ ID NO.: 1);
b) a pharmaceutical excipient; and optionally
c) a vehicle for administration, comprising a syringe or catheter, and instructional material.

* * * * *

```
                            SEQUENCE LISTING

<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Cys His Glu Ala Ser Ala Ala Gln Cys
1               5

<210> SEQ ID NO 2
<211> LENGTH: 9
<212> TYPE: PRT
<213> ORGANISM: Homo sapiens

<400> SEQUENCE: 2

Cys Ala His Ala Gln Ala Glu Ser Cys
1               5
```